United States Patent [19]

Ratzkin et al.

[11] Patent Number: 4,894,331

[45] Date of Patent: Jan. 16, 1990

[54] PARTIAL MARKER CASSETTE MUTAGENESIS OF XYLOSE ISOMERASE

[75] Inventors: Barry J. Ratzkin; Carlos A. Fisher, both of Thousand Oaks, Calif.

[73] Assignee: Amgen Inc., Thousand Oaks, Calif.

[21] Appl. No.: 781,220

[22] Filed: Sep. 27, 1985

[51] Int. Cl.[4] .................... C12P 21/00; C12P 19/24; C12N 15/00; C12N 9/92

[52] U.S. Cl. .................. 435/94; 435/172.5; 435/234; 435/320; 435/252.33; 536/27; 935/14; 935/29; 935/61

[58] Field of Search ............... 435/234, 68, 172.3, 435/94, 253, 70, 91, 170, 172.1, 233, 320, 252, 1; 536/27; 935/1, 9, 10, 11, 14, 22, 23, 27, 59, 60

[56] References Cited

U.S. PATENT DOCUMENTS

| | | | |
|---|---|---|---|
| 3,645,848 | 2/1972 | Lee et al. | 195/31 |
| 3,654,080 | 4/1972 | Bengtson et al. | 195/31 |
| 3,979,261 | 9/1976 | Outtrup | 195/65 |
| 4,687,742 | 8/1987 | Skoet et al. | 435/234 |

OTHER PUBLICATIONS

Briggs et al. 1984 EMBOJ 3(3):611–616.
Antrim et al., Applied Biochemistry & Bioengineering, 2, 97–155 (1979).
Beggs, Nature, 275, 104–109 (1979).
Hanahan, J. Mol. Biol., 166, 557–580 (1983).
Hemmingsen, Applied Biochemistry and Bioengineering, 2, 157–183 (1979).
Humphreys et al., Mol. Gen. Genet., 145, 101–108 (1976).
Kadonaga et al., Nucleic Acids Res., 13, 1733–1745 (1985).
Klee et al., BioTechnology, 3, 637–642 (1985).
Maeda et al., Nature, 315, 592–594 (1985).
Maniatis et al., Molecular Cloning, Cold Spring Harbor Laboratory, Cold Spring Harbor, New York (1982).
Sanger et al., Proc. Nat'l Acad. Sci. (U.S.A.), 74, 5463–5467 (1972).
Schellenberg et al., J. Biol. Chem, 259, 6826–6832 (1984).
Shortle, Ann. Rev. Genet., 15, 265–294 (1981).
Warburton et al., Nucleic Acids Res., 11, 5837–5854 (1983).

*Primary Examiner*—Thomas G. Wiseman
*Assistant Examiner*—Richard C. Peet
*Attorney, Agent, or Firm*—Marshall, O'Toole, Gerstein, Murray & Bicknell

[57] ABSTRACT

Constructions and methods for mutagenesis of nucleic acids involve chemical mutagenesis of a cassette comprising a structural gene linked to a non-functional restorable fragment of a marker gene. Mutants are detected by screening for the presence of the reconstituted marker among the ligation products of the cassette to a vector containing the non-functional restorable remainder of the marker gene. Xylose isomerase mutants, characterized by a change from glu (GAG) to lys (AAG) at amino acid position 262 in the xylA protein of *E. coli* were obtained by partial marker cassette mutagenesis. These mutants enzymes exhibited twice the rate of isomerization of glucose to fructose exhibited by the wild type.

16 Claims, 9 Drawing Sheets

```
CTTACTTTTGTTGCGCAATTGTACTTATTGCATTTTCTCTTCGAGGAATTACCCAGTT
TCATCATTCCATTTTATTTGCGAGCGAGGCACACTTGTGAATTATCTCAATAGCAGT
GTGAAATAACATAATTGAGCAACTGAAAGGAGTGCCCAATATTACGACACATCCATC        -33

1 MET GLN ALA TYR PHE ASP     6
ACCCGGGCATTACCTGATTATGGAGTTCAAT      1 ATG CAA GCC TAT TTT GAC    18

GLN LEU ASP ARG VAL ARG TYR GLU GLY SER LYS SER SER ASN PRO       21
CAG CTC GAT CGT GTT CGT TAT GAA GGC TCA AAA TCG TCA AAC CCG       63

LEU ALA PHE ARG HIS TYR ASN PRO ASP GLU LEU VAL LEU GLY LYS       36
TTA GCA TTC CGT CAC TAC AAT CCC GAC GAA CTG GTG TTG GGT AAG      108

ARG MET GLU HIS LEU ARG PHE ALA ALA CYS TYR TRP HIS THR           51
CGT ATG GAA CAC TTG CGT TTT GCC GCC TGC TAC TGG CAC ACC          153

PHE CYS TRP ASN GLY ALA ASP MET PHE GLY VAL GLY ALA PHE ASN       66
TTC TGC TGG AAC GGG GCA GAT ATG TTT GGT GTG GGG GCG TTT AAT      198

ARG PRO TRP GLN GLN PRO GLY GLU ALA LEU ALA LEU ALA LYS ARG       81
CGT CCG TGG CAG CAG CCT GGT GAG GCA CTG GCG TTG GCG AAG CGT      243
```

FIG. 7 CONT.

```
LYS ALA ASP VAL ALA PHE GLU PHE PHE HIS LYS LEU HIS VAL PRO      96
AAA GCA GAT GTC GCA TTT GAG TTT TTC CAC AAG TTA CAT GTG CCA     288

PHE TYR CYS PHE HIS ASP VAL ASP VAL SER PRO GLU GLY ALA SER     111
TTT TAT TGC TTC CAC GAT GTT GAT GTT TCC CCT GAG GGC CCG TCG     333

LEU LYS GLU TYR ILE ASN ASN PHE ALA GLN MET VAL ASP VAL LEU     126
TTA AAA GAG TAC ATC AAT AAT TTT GCG CAA ATG GTT GAT GTC CTG     378

ALA GLY LYS GLN GLU SER GLY VAL LYS LEU LEU TRP GLY THR         141
GCA GGC AAG CAA GAA AGC GGC GTG AAG CTG CTG TGG GGA ACG         423

ALA ASN CYS PHE THR ASN PRO ARG TYR GLY ALA ALA THR             156
GCC AAC TGC TTT ACA AAC CCT CGC TAC GGC GCG GCG ACG             468

ASN PRO ASP GLU VAL PHE SER TRP ALA THR GLN VAL VAL             171
AAC CCA GAT GAA GTC TTC AGC TGG GCA ACG CAA GTT GTT             513
                              PvuII

THR ALA MET GLU ALA THR HIS LYS LEU GLY GLY GLU ASN TYR VAL     186
ACA GCG ATG GAA GCA ACC CAT AAA TTG GGT GAA AAC TAT GTC         558

LEU TRP GLY ARG GLY TYR GLU GLY THR LEU ASN THR ASP             201
CTG TGG GGT CGT GGA TAC GAA ACG TTA AAT ACC GAC                 603

LEU ARG GLN GLU ARG GLY LEU GLN PHE MET VAL                     216
TTG CGT CAG GAA CGT GGC GAA CAG TTT ATG GTG                     648
```

FIG. 7 CONT.'

| | | | |
|---|---|---|---|
| LEU CTG | PHE TTT | TYR TAC | GLY GGT | HIS CAT | ILE ATC | GLY GGC | ALA GCG | MET ATG | ASP GAT | THR ACG | MET ATG | ALA GCA | LEU CTG | ALA GCG | 366 1098 |
| LEU CTG | LYS AAA | ILE ATT | ALA GCA | ALA GCG | ARG CGC | MET ATG | ILE ATT | GLU GAA | ASP GAT | GLY GGC | LEU CTG | GLU GAG | ASP GAT | LYS AAA | 381 1143 |
| ARG CGC | ILE ATC | ALA GCG | GLN CAG | ARG CGT | TYR TAT | SER TCC | GLY GGC | TRP TGG | ASN AAT | SER AGC | GLU GAA | LEU TTG | GLY GGC | GLN CAG | 396 1188 |
| GLN CAA | ILE ATC | LEU CTG | LYS AAA | GLY GGC | GLN CAA | MET ATG | SER TCA | LEU CTG | ALA GCA | ASP GAT | LEU TTA | ALA GCC | LYS AAA | TYR TAT | 411 1233 |
| ALA GCT | GLN CAG | HIS GAA | HIS CAT | LEU TTG | SER TCT | PRO CCG | VAL GTG | HIS CAT | GLN CAG | SER AGT | GLY GGT | ARG CGC | GLN CAG | | 426 1278 |
| GLU GAA | GLN CAA | LEU CTG | GLU GAA | ASN AAT | LEU CTG | VAL GTA | ASN AAC | HIS CAT | TYR TAT | LEU CTG | PHE TTC | ASP GAC | LYS AAA | | 440 1320 |

OC
TAACGGCTAACTGTGCAGTCCGTTGGCCCGGTTATCGGTAGGATACCGGGCATTTTTT 1383

TAAGGAACGATCGATATGTATAT

FIG. 7 CONT.

| | | | | | | | | | | | | | | | |
|---|---|---|---|---|---|---|---|---|---|---|---|---|---|---|---|
| VAL | GLU | HIS | LYS | ILE | GLY | PHE | GLN | GLY | THR | LEU | LEU | ILE | | 231 | |
| GTT | GAG | CAT | AAA | ATC | GGT | TTC | CAG | GGC | ACG | TTG | CTT | ATC | | 693 | |
| GLU | PRO | LYS | PRO | GLN | PRO | THR | LYS | HIS | GLN | TYR | ASP | | | 246 | |
| GAA | CCG | AAA | CCG | CAA | CCG | ACC | AAA | CAT | CAA | TAT | GAT | | | 738 | |
| ALA | ALA | THR | VAL | TYR | GLY | PHE | LEU | LYS | GLN | PHE | GLU | LYS | | 261 | |
| GCC | GCG | ACG | GTC | TAT | GGC | TTC | CTG | AAA | CAG | TTT | GAA | AAA | | 783 | |
| GLU | ILE | LYS | LEU | ASN | ILE | GLU | ALA | ASN | ARG | GLY | LEU | ALA | GLY | 276 | |
| GAG | ATT | AAA | CTG | AAC | ATT | GAA | GCT | AAC | CGT | GGC | CTG | GCA | GGT | 828 | |
| HIS | SER | PHE | HIS | HIS | GLU | ILE | ALA | THR | ALA | ILE | ALA | LEU | | 291 | |
| CAC | TCT | TTC | CAT | CAT | GAA | ATA | GCC | ACG | GCG | ATT | GCG | CTT | | 873 | |
| PHE | GLY | SER | VAL | ASP | ALA | ALA | ASN | ARG | GLY | ASP | ALA | GLN | LEU | 306 | GLY |
| TTC | GGT | TCT | GTC | GAC | GCC | AAC | CGT | GGC | GAT | GCG | CAA | CTG | | 918 | GGC |
| | | | | Sal I | | | | | | | | | | | |
| ASP | THR | ASP | GLN | PHE | PRO | ASN | SER | VAL | GLU | ASN | ALA | LEU | VAL | 321 | |
| GAC | ACC | GAC | CAG | TTC | CCG | AAC | AGT | GTG | GAA | AAT | GCG | CTG | GTG | 963 | |
| MET | TYR | GLU | ILE | LEU | LYS | ALA | GLY | GLY | PHE | THR | THR | GLY | LEU | 336 | |
| ATG | TAT | GAA | ATT | CTC | AAA | GCA | GGC | GGT | TTC | ACC | ACC | GGT | CTG | 1008 | |
| ASN | PHE | ASP | ALA | LYS | VAL | ARG | ARG | GLN | SER | THR | ASP | LYS | TYR | 351 | ASP |
| AAC | TTC | GAT | GCC | AAA | GTA | CGT | CGT | CAA | AGT | ACT | GAT | AAA | TAT | 1053 | GAT |

PARTIAL MARKER CASSETTE MUTAGENESIS OF XYLOSE ISOMERASE

BACKGROUND

The present invention relates in general to constructions and methods for cassette mutagenesis and in particular to constructions and methods for partial marker cassette mutagenesis of xylose isomerase.

Enzymes have been used extensively in industrial processes for over 100 years since the introduction of the use of trypsin in the processing of animal skins into leather. Presently, enzymes are employed in many processes from the microgram scale of medical diagnostic tests to the billion pound scale of high fructose corn syrup production. It is because of their specificity as well as the mildness of their reaction conditions of temperature and pressure that enzymes are readily used in industrial processes.

Nevertheless, a high degree of specificity limits the usefulness of some enzymes. Reaction condition limitations such as pH, temperature, ionic strength and ionic environment limit the range of many enzymes. In some industrial processes, a sequential use of different enzymes dictates that new conditions be established at each new enzymatic step. These extra manipulations can lead to extra costs, especially at the million pound scale.

Traditionally, one would search for an enzyme having more desirable specificity or a greater reaction condition tolerance by screening for the enzyme in naturally occurring microorganisms. Such a search is time consuming and labor intensive. Ideally, one would like to design a protein de novo or at least modify existing ones by mutagenesis so that their activities would match the process specifications.

There exist a number of techniques for the mutagenesis of nucleic acids. The techniques for mutagenesis of polynucleotides, such as genes, may be divided into techniques for deletion mutagenesis, techniques for insertion mutagenesis and techniques for base substitution mutagenesis. Deletion and insertion mutagenesis are generally employed to locate functional elements or protein coding regions of a genome. Shortle, *Ann. Rev. Genet.*, 15, 265–94 (1981). Base substitution mutagenesis is a preferred method of mutagenizing an identified structural gene.

Base substitution mutagenesis may be performed by random chemical or physical mutation or by site-directed mutagenesis employing oligonucleotides synthesized to partially match a nucleotide sequence within a target nucleotide sequence. Random mutagenesis is preferred in any situation where, because of insufficient understanding of the system being studied, there is no obvious rationale for specific base substitutions. Kadonaga et al., *Nucleic Acids Res.*, 13, 1733–1745 (1985). The strategy for random mutagenesis involves exposing a large number of copies of a target sequence to a mutagen and then screening for the presence of mutants.

A polynucleotide may be prepared for mutagenesis by inserting it into a vector such as a circular, double-stranded DNA structure called a plasmid (Humphreys et al., *Molec. Gen. Genet.*, 145, 101–108 (1976)), or such as a virus (Kadonaga et al., supra), both of which replicate independently of the chromosomal DNA that forms the bulk of the hereditary material in a cell. However, the presence of a large amount of plasmid or viral DNA reduces the efficiency of the mutagen by providing a much larger target, most of which is not intended to be mutagenized, and by increasing the probability of missing desired mutations due to deleterious effects resulting from mutagenesis of the vector.

The size of the target presented to a mutagen may be reduced by exposing only the polynucleotide to be mutagenized to the mutagen. Warburton et al., *Nucleic Acids Res.*, 11, 5837–5854 (1983). Where the polynucleotide to be mutagenized is a trp promoter sequence, fusing the mutagenized polynucleotide in phase to a lac Z $\alpha$ fragment region in a phage M13 vector permits mutants to be scored based upon the expression of the $\beta$-galactosidase gene, which is detected as an abnormal intensity of blue color in M13 plaques in agar containing 5-bromo4-chloroindoxyl-$\beta$-D-galactoside. Warburton et al., supra. However, the detection of mutants by a cooperative interaction between the mutagenized polynucleotide and a vector-borne label is of limited applicability and is not directly applicable to the mutagenesis of structural genes.

In fact, a major problem with in vitro mutagenesis in general is the absence of a simple method for the screening of mutants in a wild-type background. Kadonaga et al., supra. Although this problem may be avoided by using a very high level of mutagenesis, multiple base substitutions tend to occur which are less desirable for the unambiguous interpretation of mutant phenotypes than are single or double nucleotide substitutions. Kadonaga at al., supra.

SUMMARY OF THE INVENTION

The present invention provides a method for mutagenizing a segment of a nucleic acid which comprises the steps of linking a nucleic acid segment to be mutagenized to at least a portion of a marker gene; forming a partial marker cassette by isolating the nucleic acid segment and a nonfunctional restorable portion of the marker gene; exposing the partial marker cassette to a mutagen; ligating the partial marker cassette to a vector containing a nonfunctional restorable remainder of the marker gene thereby restoring the function of the marker gene; and screening for the presence of the marker. This method may involve ligating the nucleic acid into a restriction site linked to the marker gene and may involve chemically mutagenizing the partial marker cassette.

The present invention also provides a construction for the mutagenesis of a nucleic acid including a polynucleotide to be mutagenized and a nonfunctional restorable portion of a detectable marker gene linked to the polynucleotide. This construction may include a polynucleotide which is a structural gene that may be the gene encoding xylose isomerase. Specifically, the gene encoding xylose isomerase may be the xylA gene of *E. coli*. The detectable marker gene may be a gene encoding an enzyme conferring resistance to an antibiotic. Specifically, the antibiotic may be kanamycin. The construction may further include a partial marker casette vector comprising a nonfunctional restorable remainder of the marker gene present in the partial marker cassette. In the construction, a restriction site may occur at a boundary separating the portion from the remainder.

The present invention further provides a construction for the mutagenesis of a xylose isomerase including a polynucleotide encoding the xylA gene of *E. coli*, a nonfunctional restorable portion of a kanamycin resistance gene of *E. coli* linked to the polynucleotide, and a vector comprising a nonfunctional restorable remainder of the kanamycin resistance gene linked to the portion and having a restriction site at a boundary separating the portion from the remainder.

In addition, the present invention provides a structural gene which, when inserted in an appropriate vector used to transform an appropriate host, is capable of expressing an enzyme which isomerizes glucose to fructose and which is characterized by the presence of an adenosine residue at position 784 of the nucleotide sequence as given in Table I and is also characterized as having a nucleotide sequence sufficiently similar to the nucleotide sequence of Table I to permit the enzyme to isomerize glucose to fructose. Specifically, the structural gene may be a gene having a nucleotide sequence 3' to nucleotide sequence position 298 which is identical to nucleotide sequence given in Table I 3' to nucleotide position 297, except for the substitution of an adenosine residue for a guanidine residue at position 784. This structural gene may be the plasmid-borne mutant xylA gene as found in ATCC No. 53274 or the structural gene may be the plasmid-borne mutant xylA gene as found in ATCC No. 53275.

A xylose isomerase enzyme according to the present invention is characterized by the presence of a lysine residue at position 262 of the amino acid sequence as given in Table I and is further characterized as being sufficiently similar in amino acid sequence to the rest of Table I capable of isomerizing gluctose to fructose. Specifically, the xylose isomerase enzyme may have an amino acid sequence from amino acid residue 100 to the carboxyl terminus which is identical to the amino acid sequence given in Table I except for the substitution of lys for glu at amino acid position 262. More specifically, the xylose isomerase enzyme may be the expression product of the plasmid-borne mutant xylA gene as found in ATCC No. 53274 or may be the expression product of the plasmid-borne mutant xylA gene as found in ATCC No. 53275.

The present invention provides a method for the isomerization of a monosaccharide which comprises the step of exposing the monosaccharide to a xylose isomerase enzyme characterized by the presence of a lysine residue at position 262 of the amino acid sequence as given in Table I and further characterized as being capable of isomerizing glucose to fructose under appropriate conditions for the isomerization of the monosaccharide. The amino acid sequence of the enzyme from amino acid residue 100 to the carboxyl terminus may be identical to the amino acid sequence given in Table I except for the substitution of lys for glu at position 262. The enzyme may comprise the expression product of the plasmid-borne mutant xylA gene as found in ATCC No. 53274, or may comprise the expression product of the plasmid-borne mutant xylA gene as found in ATCC No. 53275. The monosaccharide may be glucose or xylose.

DETAILED DESCRIPTION

The present invention provides methods and constructions for introducing random mutations into a particular gene.

Figure 1:
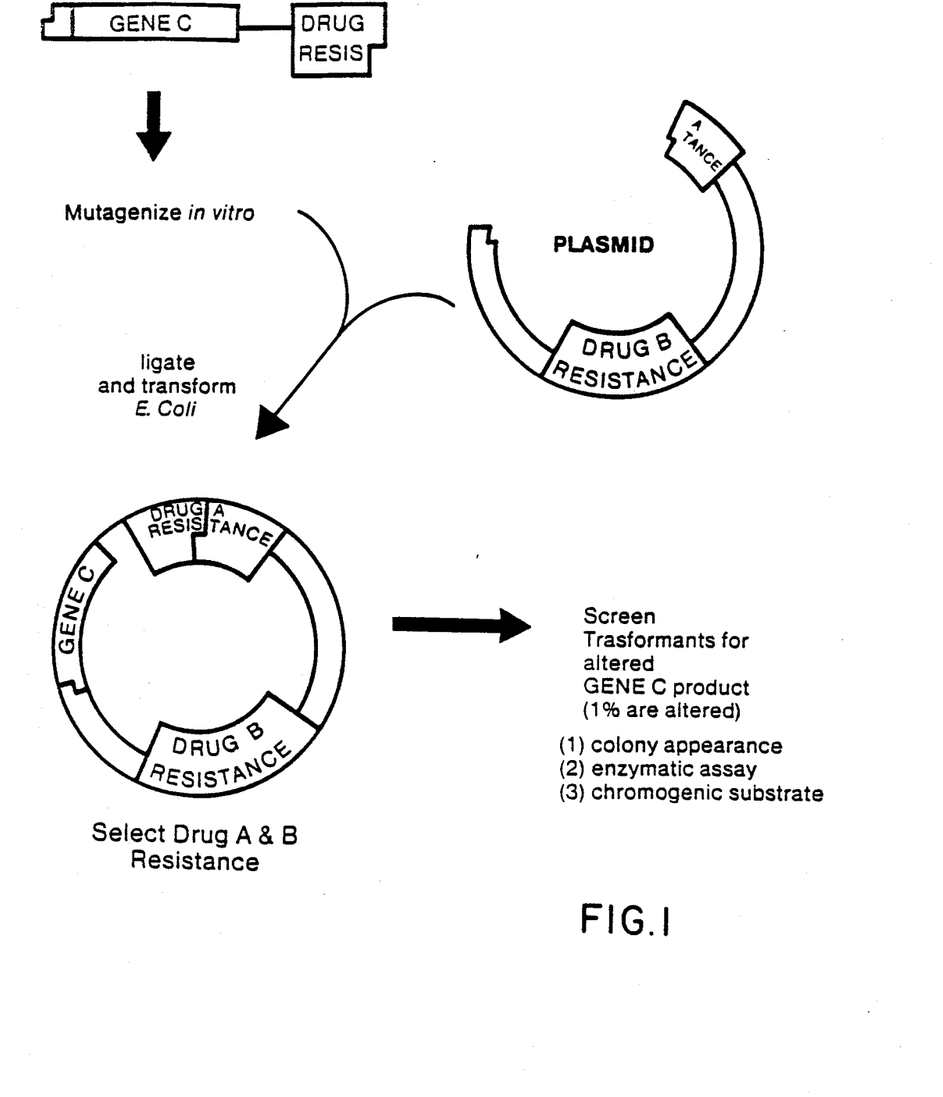
FIG. 1 is a flow chart illustrating a first variation of a method of partial marker cassette mutagenesis according to the present invention.

As illustrated in FIG. 1, a method for partial marker cassette mutagenesis according to the present invention involves mutagenizing an isolated gene (C) which is linked to a non-functional part of a selectable marker gene (drug resistance A) in a cassette. After completion of mutagenesis, the cassette is then ligated to a plasmid containing the non-functional remainder of the selectable marker gene (drug resistance A) so that a functional marker gene is obtained. Either direct selection or an in situ colony assay may be used to determine the presence of modified enzymatic activity of gene C. This method directs mutagenesis to a particular gene without prejudicing selection for a particular mutant allele. Thus, any kind of aberration including those which render gene C non-functional, may be scored after the initial selection of drug resistance.

As also illustrated in FIG. 1, the plasmid into which mutagenized gene C is introduced may contain a second selectable marker gene. Use of a second marker in this way reduces artifacts by introducing a second selection criteron for transformants. Specifically, the use of a second marker permits the identification of transformants containing plasmids which do not include the mutant gene.

In general, the present invention randomly introduces mutations into a protein after which the function of altered proteins is examined. A collection of mutations, whether they are active or inactive, may be used to map catalytically active areas of the protein.

The present invention has a particular advantage over mutagenesis schemes in which the polynucleotide sequence to be mutagenized is linked to a complete marker and possibly to additional genes. By limiting the target for a mutagen to the nucleic acid to be mutagenized plus only a portion of a marker, which may be located 5' or 3' to the target as convenient, the efficiency of a mutagen is enhanced and the likelihood of inducing undesired mutations is reduced. The probability of mutagenizing only the target sequence may be increased by minimizing the size of the portion of the marker included in the partial marker cassette.

Among the commercially useful genes which are potentially most interesting candidates for mutagenesis is the xylA gene of *E. coli* which encodes for a protein called xylose isomerase. While the xylA gene product is required for xylose fermentation, like other xylose isomerases, the product of the xylA gene also isomerizes glucose. Lee et al., U.S. Pat. No. 3,645,848; and Bengtson et al., U.S. Pat. No. 3,654,080. Several types of xylose isomerases are used to produce high fructose corn syrup.

All of the fructose corn syrup in the United States is produced using immobilized enzyme technology and the isomerization of glucose to fructose in the production of corn syrup represents the largest commercial application of an immobilized enzyme. Antrim et al., *Applied Biochemistry and Bioengineering*, 2, 97–155 1979. Despite the availability of four different glucose isomerizing enzymes, the only enzyme that is commercially important for the isomerization of glucose to fructose is D-xylose isomerase. Antrim et al., supra.

Although the properties of presently available xylose isomerases are subject to improvement, particularly with regard to thermal stability and the effect of pH and temperature on activity, the search for improved forms of xylose isomerase has primarily been pursued by searching for new strains of microorganisms which possess enzymes having desired qualities. See e.g., Outtrup, U.S. Pat. No. 3,979,261.

Accordingly the present invention is exemplified by the partial marker cassette mutagenesis of the xylA gene of *E. coli*. In Example 1, a partial marker cassette containing the xylA gene at *E. coli* is mutagenized. In Example 2, mutants produced according to Example 1 are analyzed for the synthesis of xylA protein and for xylose isomerase activity. In Example 3, the solubilities of mutant xylA proteins extracted in Example 2 are determined. Finally, in Example 4, the mutant xylA genes of the mutant strains identified in Example 1 are partially sequenced.

EXAMPLE 1

The xylA gene of *E. coli* is located in the xyl operon which is carried by the plasmid pLCl-3 that is part of the Clark and Carbon bank (available through the *E. coli* Genetic Stock Center, Yale University, New Haven, Conn.). The xylA gene, is located on a 1.6 kb BglII fragment. Schellenberg, et al., *J. Biol. Chem.*, 259, 6826–6832 (1984). The 1.6 kb fragment was obtained by BglII [as obtained from Bethesda Research Laboratories (BRL), Inc., Rockville, Md.] digestion of pLCl-3 separated by agarose gel electrophoresis and identified in a band stained with ethidium bromide. The band was excised from the gel and the 1.6 kb fragment was washed free of the gel.

Figure 7:
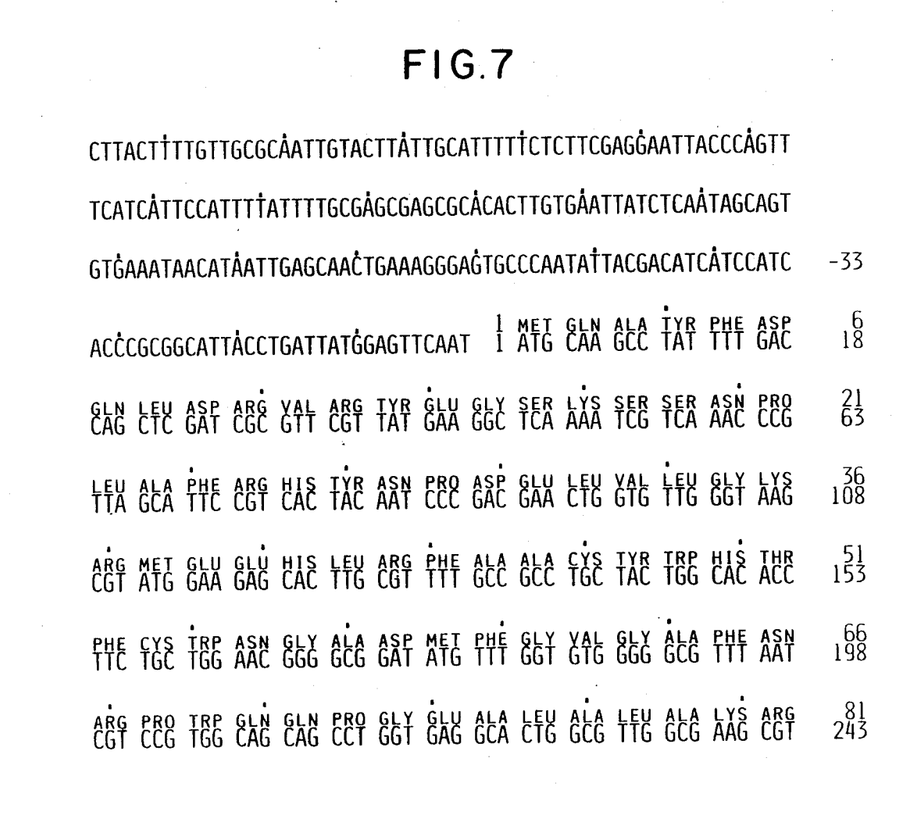

This BglII fragment in the DNA sequence, a single strand of which is given in FIG. 7, contains all the signals needed for induction of xylA by xylose. The BglII fragment was cloned into the BamHI site of pBR322 [the complete nucleotide sequence for which is provided in Sutcliffe, *Cold Spring Harbor Symp. Quant. Biol.*, 43, 77–90 (1979)] to create plasmid pCF313. pBR322 was digested with BamHI (BRL) and phosphatased using bacterial alkaline phosphatase (BAP) [BRL]. After determining that digestion was complete by agarose gel electrophoresis, the phosphatased BamHI fragment of pBR322 and the 1.6 kb xylA fragment were introduced into a T4 ligase buffer (66 mM Tris-HCl, pH 7.8; 6.6 mM $MgCl_2$; 10 mM DTT; and 0.3 mM ATP) containing T4 DNA ligase (BRL). Cells of *E. coli* bacterial strain JA221 were exposed to products of this ligation in a transformation reaction according to the transformation procedure of Hanahan, *J. Mol. Biol.*, 166, 557–580 (1983). Cells from the transformation reaction were plated onto EMB medium (as available from Difco, Detroit, Mich.) containing 2% xylose and 50 µg/ml ampicillin (Calbiochem, San Diego, Calif.). DNA was isolated from resulting colonies of all types. The isolated DNA was subjected to restriction endonuclease analysis on agarose gels and the corresponding transformants were characterized thereby.

TABLE I

CTTACTTTTGTTGCGCAATTGTACTTATTGCATTTTTCTCTTCGAGGAATTACCCAGTT

TCATCATTCCATTTTATTTTGCGAGCGAGCGCACACTTGTGAATTATCTCAATAGCAGT

GTGAAATAACATAATTGAGCAACTGAAAGGGAGTGCCCAATATTACGACATCATCCATC   −33

|  |  |  |
|---|---|---|
| ACCCGCGGCATTACCTGATTATGGAGTTCAAT | 1 met gln ala tyr phe asp<br>1 ATG CAA GCC TAT TTT GAC | 6<br>18 |
| | gln leu asp arg val arg tyr glu gly ser lys ser ser asn pro<br>CAG CTC GAT CGC GTT CGT TAT GAA GGC TCA AAA TCG TCA AAC CCG | 21<br>63 |
| | leu ala phe arg his tyr asn pro asp glu leu val leu gly lys<br>TTA GCA TTC CGT CAC TAC AAT CCC GAC GAA CTG GTG TTG GGT AAG | 36<br>108 |
| | arg met glu glu his leu arg phe ala ala cys tyr trp his thr<br>CGT ATG GAA GAG CAC TTG CGT TTT GCC GCC TGC TAC TGG CAC ACC | 51<br>153 |
| | phe cys trp asn gly ala asp met phe gly val gly ala phe asn<br>TTC TGC TGG AAC GGG GCG GAT ATG TTT GGT GTG GGG GCG TTT AAT | 66<br>198 |
| | arg pro trp gln gln pro gly glu ala leu ala leu ala lys arg<br>CGT CCG TGG CAG CAG CCT GGT GAG GCA CTG GCG TTG GCG AAG CGT | 81<br>243 |
| | lys ala asp val ala phe glu phe phe his lys leu his val pro<br>AAA GCA GAT GTC GCA TTT GAG TTT TTC CAC AAG TTA CAT GTG CCA | 96<br>288 |

TABLE I-continued

| | | | | | | | | | | | | | | | |
|---|---|---|---|---|---|---|---|---|---|---|---|---|---|---|---|
| phe | tyr | cys | phe | his | asp | val | asp | val | ser | pro | glu | gly | ala | ser | 111 |
| TTT | TAT | TGC | TTC | CAC | GAT | GTG | GAT | GTT | TCC | CCT | GAG | GGC | CCG | TCG | 333 |

| | | | | | | | | | | | | | | | |
|---|---|---|---|---|---|---|---|---|---|---|---|---|---|---|---|
| leu | lys | glu | tyr | ile | asn | asn | phe | ala | gln | met | val | asp | val | leu | 126 |
| TTA | AAA | GAG | TAC | ATC | AAT | AAT | TTT | GCG | CAA | ATG | GTT | GAT | GTC | CTG | 378 |

| | | | | | | | | | | | | | | | |
|---|---|---|---|---|---|---|---|---|---|---|---|---|---|---|---|
| ala | gly | lys | gln | glu | glu | ser | gly | val | lys | leu | leu | trp | gly | thr | 141 |
| GCA | GGC | AAG | CAA | GAA | GAG | AGC | GGC | GTG | AAG | CTG | CTG | TGG | GGA | ACG | 423 |

| | | | | | | | | | | | | | | | |
|---|---|---|---|---|---|---|---|---|---|---|---|---|---|---|---|
| ala | asn | cys | phe | thr | asn | pro | arg | tyr | gly | ala | gly | ala | ala | thr | 156 |
| GCC | AAC | TGC | TTT | ACA | AAC | CCT | CGC | TAC | GGC | GCG | GGT | GCG | GCG | ACG | 468 |

| | | | | | | | | | | | | | | | |
|---|---|---|---|---|---|---|---|---|---|---|---|---|---|---|---|
| asn | pro | asp | pro | glu | val | phe | ser | trp | ala | ala | thr | gln | val | val | 171 |
| AAC | CCA | GAT | CCT | GAA | GTC | TTC | AGC | TGG | GCG | GCA | ACG | CAA | GTT | GTT | 513 |
| | | | | | | PvuII | | | | | | | | | |

| | | | | | | | | | | | | | | | |
|---|---|---|---|---|---|---|---|---|---|---|---|---|---|---|---|
| thr | ala | met | glu | ala | thr | his | lys | leu | gly | gly | glu | asn | tyr | val | 186 |
| ACA | GCG | ATG | GAA | GCA | ACC | CAT | AAA | TTG | GGC | GGT | GAA | AAC | TAT | GTC | 558 |

| | | | | | | | | | | | | | | | |
|---|---|---|---|---|---|---|---|---|---|---|---|---|---|---|---|
| leu | trp | gly | gly | arg | glu | gly | tyr | glu | thr | leu | leu | asn | thr | asp | 201 |
| CTG | TGG | GGC | GGT | CGT | GAA | GGT | TAC | GAA | ACG | CTG | TTA | AAT | ACC | GAC | 603 |

| | | | | | | | | | | | | | | | |
|---|---|---|---|---|---|---|---|---|---|---|---|---|---|---|---|
| leu | arg | gln | glu | arg | glu | gln | leu | gly | arg | phe | met | gln | met | val | 216 |
| TTG | CGT | CAG | GAG | CGT | GAA | CAA | CTG | GGC | CGC | TTT | ATG | CAG | ATG | GTG | 648 |

| | | | | | | | | | | | | | | | |
|---|---|---|---|---|---|---|---|---|---|---|---|---|---|---|---|
| val | glu | his | lys | his | lys | ile | gly | phe | gln | gly | thr | leu | leu | ile | 231 |
| GTT | GAG | CAT | AAA | CAT | AAA | ATC | GGT | TTC | CAG | GGC | ACG | TTG | CTT | ATC | 693 |

| | | | | | | | | | | | | | | | |
|---|---|---|---|---|---|---|---|---|---|---|---|---|---|---|---|
| glu | pro | lys | pro | gln | glu | pro | thr | lys | his | gln | tyr | asp | tyr | asp | 246 |
| GAA | CCG | AAA | CCG | CAA | GAA | CCG | ACC | AAA | CAT | CAA | TAT | GAT | TAC | GAT | 738 |

| | | | | | | | | | | | | | | | |
|---|---|---|---|---|---|---|---|---|---|---|---|---|---|---|---|
| ala | ala | thr | val | tyr | gly | phe | leu | lys | gln | phe | gly | leu | glu | lys | 261 |
| GCC | GCG | ACG | GTC | TAT | GGC | TTC | CTG | AAA | CAG | TTT | GGT | CTG | GAA | AAA | 783 |

| | | | | | | | | | | | | | | | |
|---|---|---|---|---|---|---|---|---|---|---|---|---|---|---|---|
| glu | ile | lys | leu | asn | ile | glu | ala | asn | his | ala | thr | leu | ala | gly | 276 |
| GAG | ATT | AAA | CTG | AAC | ATT | GAA | GCT | AAC | CAC | GCG | ACG | CTG | GCA | GGT | 828 |

| | | | | | | | | | | | | | | | |
|---|---|---|---|---|---|---|---|---|---|---|---|---|---|---|---|
| his | ser | phe | his | his | glu | ile | ala | thr | ala | ile | ala | leu | gly | leu | 291 |
| CAC | TCT | TTC | CAT | CAT | GAA | ATA | GCC | ACC | GCC | ATT | GCG | CTT | GGC | CTG | 873 |

| | | | | | | | | | | | | | | | |
|---|---|---|---|---|---|---|---|---|---|---|---|---|---|---|---|
| phe | gly | ser | val | asp | ala | asn | arg | gly | asp | ala | gln | leu | gly | trp | 306 |
| TTC | GGT | TCT | GTC | GAC | GCC | AAC | CGT | GGC | GAT | GCG | CAA | CTG | GGC | TGG | 918 |
| | | | | SalI | | | | | | | | | | | |

| | | | | | | | | | | | | | | | |
|---|---|---|---|---|---|---|---|---|---|---|---|---|---|---|---|
| asp | thr | asp | gln | phe | pro | asn | ser | val | glu | glu | asn | ala | leu | val | 321 |
| GAC | ACC | GAC | CAG | TTC | CCG | AAC | AGT | GTG | GAA | GAG | AAT | GCG | CTG | GTG | 963 |

| | | | | | | | | | | | | | | | |
|---|---|---|---|---|---|---|---|---|---|---|---|---|---|---|---|
| met | tyr | glu | ile | leu | lys | ala | gly | gly | phe | thr | thr | gly | gly | leu | 336 |
| ATG | TAT | GAA | ATT | CTC | AAA | GCA | GGC | GGT | TTC | ACC | ACC | GGT | GGT | CTG | 1008 |

| | | | | | | | | | | | | | | | |
|---|---|---|---|---|---|---|---|---|---|---|---|---|---|---|---|
| asn | phe | asp | ala | lys | val | arg | arg | gln | ser | thr | asp | lys | tyr | asp | 351 |
| AAC | TTC | GAT | GCC | AAA | GTA | CGT | CGT | CAA | AGT | ACT | GAT | AAA | TAT | GAT | 1053 |

| | | | | | | | | | | | | | | | |
|---|---|---|---|---|---|---|---|---|---|---|---|---|---|---|---|
| leu | phe | tyr | gly | his | ile | gly | ala | met | asp | thr | met | ala | leu | ala | 366 |
| CTG | TTT | TAC | GGT | CAT | ATC | GGC | GCG | ATG | GAT | ACG | ATG | GCA | CTG | GCG | 1098 |

| | | | | | | | | | | | | | | | |
|---|---|---|---|---|---|---|---|---|---|---|---|---|---|---|---|
| leu | lys | ile | ala | ala | arg | met | ile | glu | asp | gly | glu | leu | asp | lys | 381 |
| CTG | AAA | ATT | GCA | GCG | CGC | ATG | ATT | GAA | GAT | GGC | GAG | CTG | GAT | AAA | 1143 |

TABLE I-continued

```
arg  ile  ala  gln  arg  tyr  ser  gly  trp  asn  ser  glu  leu  gly  gln           396
CGC  ATC  GCG  CAG  CGT  TAT  TCC  GGC  TGG  AAT  AGC  GAA  TTG  GGC  CAG          1188 gln  ile  leu  lys  gly  gln  met  ser  leu  ala  asp  leu  ala  lys  tyr           411
CAA  ATC  CTG  AAA  GGC  CAA  ATG  TCA  CTG  GCA  GAT  TTA  GCC  AAA  TAT          1233 ala  gln  glu  his  his  leu  ser  pro  val  his  gln  ser  gly  arg  gln           426
GCT  CAG  GAA  CAT  CAT  TTG  TCT  CCG  GTG  CAT  CAG  AGT  GGT  CGC  CAG          1278 glu  gln  leu  glu  asn  leu  val  asn  his  tyr  leu  phe  asp  lys                440
GAA  CAA  CTG  GAA  AAT  CTG  GTA  AAC  CAT  TAT  CTG  TTC  GAC  AAA               1320

OC
TAACGGCTAACTGTGCAGTCCGTTGGCCCGGTTATCGGTAGCGATACCGGGCATTTTT                         1383

TAAGGAACGATCGATATGTATAT
```

Figure 2:
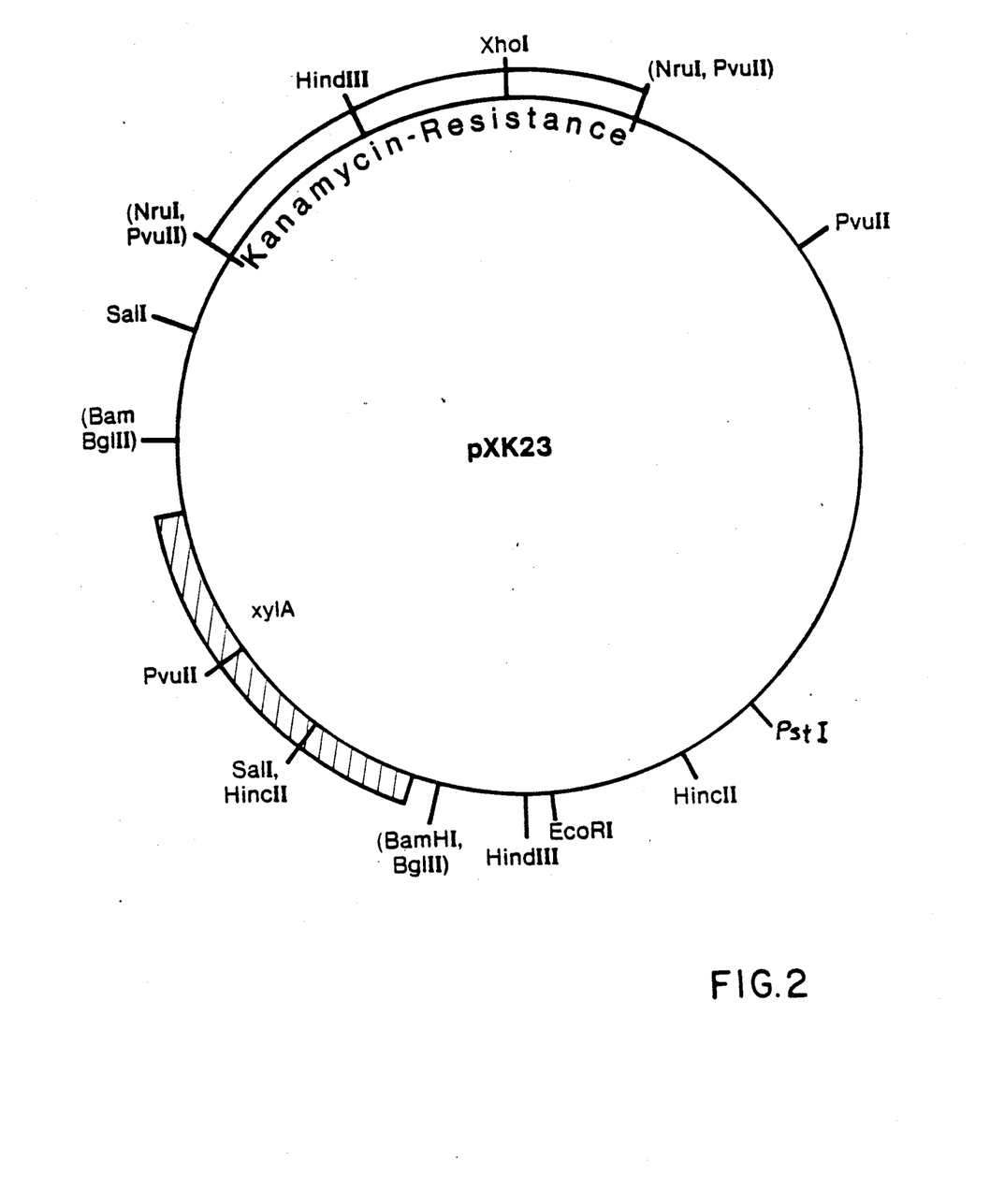
FIG. 2 is a partial restriction map of the plasmid pXK23 which is useful for partial marker cassette mutagenesis of xylose isomerase according to the present invention.

Subsequently, a 1.7 kb PvuII piece containing an $E.$ $coli$ kanamycin resistance gene from transposon Tn 903 [the complete nucleotide sequence for which is provided in Oka, et al., $J.$ $Mol.$ $Biol.,$ 147, 217–226 (1981)] was isolated from pCR1 and was inserted into the NruI site (derived from pBR322 at position 972 thereof) of pCF313 by digestion with NruI (BRL) and ligation (as above) to create plasmid pXK23 as illustrated in FIG. 2. A partial marker cassette was formed from pXK23 by HindIII (BRL) digestion. The resulting 3.2 kb HindIII fragment runs from the middle of the kanamycin-resistance gene, forming a partial marker, to beyond the 3' end of the xylA gene as found in pXK23. This kanamycin-resistance partial marker is not functional to confer kanamycin-resistance but the ability to confer kanamycin-resistance may be restored by ligation of the partial marker to the remainder of the kanamycin-resistance gene in proper orientation.

Figure 6:
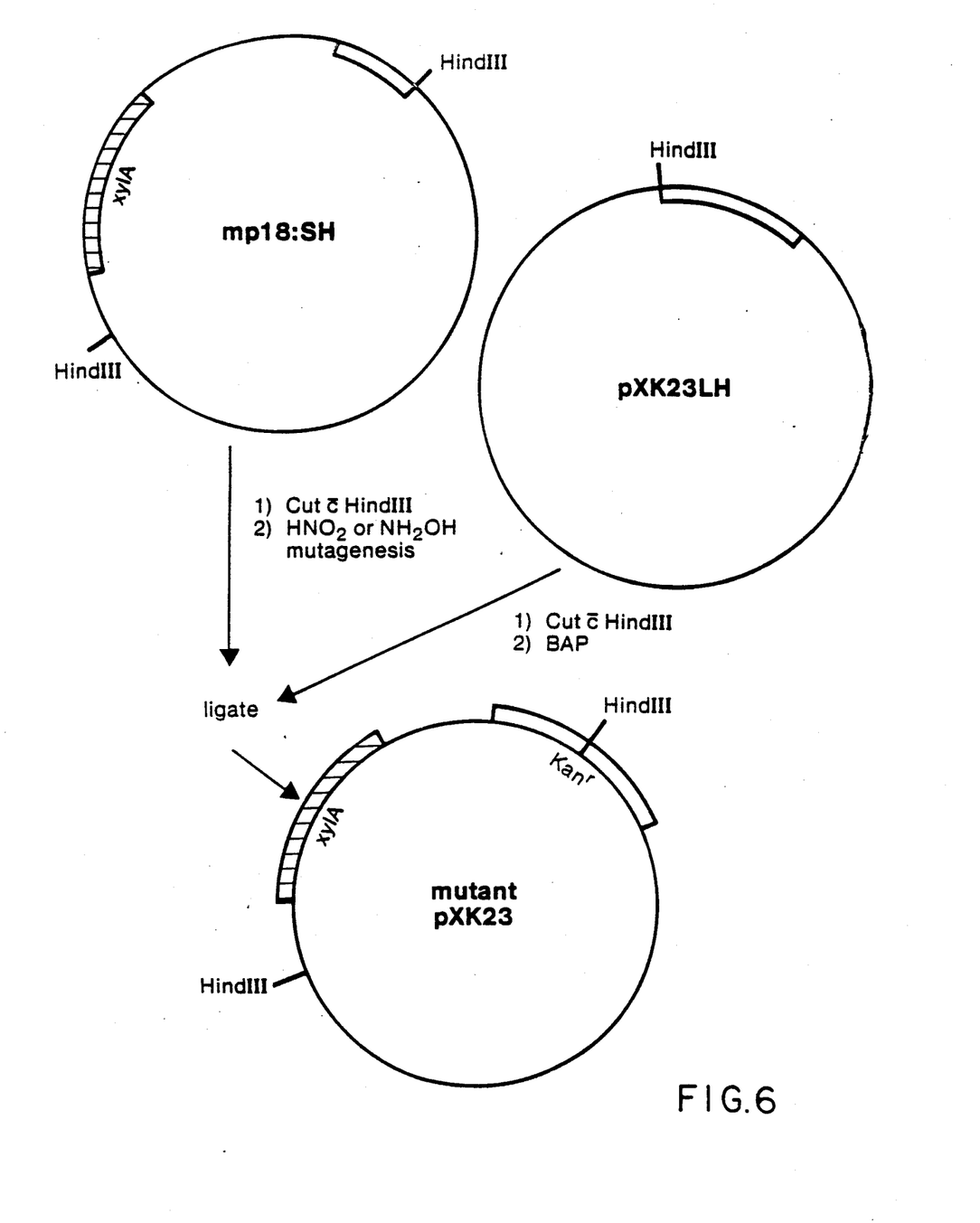
FIG. 6 is a flow chart illustrating a second variation of a method for partial marker cassette mutagenesis according to the present invention and FIG. 7 illustrates the nucleotide sequence of a single strand of a BglII fragment containing the xylA gene.

A 3.2 kb HindII fragment was purified from a digest of pXK23. This fragment was mutagenized with 70 mM $NaNO_2$ in the presence of 2 mM spermine and in 33 mM sodium acetate (pH 4.6) [Warburton, et al., $Nucleic$ $Acid$ $Res.,$ 11, 5837–5854 (1983)] for 30, 60 or 90 minutes at 30° C., neutralized, the DNA was precipitated with ethanol and ligated to the large HindIII fragment of pXK23 (i.e., to pXK23LH as shown in FIG. 6). Consequently, pXK23LH constitutes a vector for partial marker cassette mutagenesis inasmuch as it contains the remainder of the kanamycin-resistance gene which, when ligated in proper orientation to the kanamycin-resistance partial marker in the 3.2 kb HindIII fragment, restores an ability to confer kanamycin resistance.

Additionally, unmutagenized xylA fragment ligated to pXK23LH ("Control Lig.") and uncut pXK23 plasmid were used in two control transformations.

Ligation products were screened by transformation (Hanahan, supra) of cells of $E.$ $coli$ strain RR1 (xyllA5), which has a xylose-negative phenotype (Schellenberg et al, supra; for characterization of strain RR1 see e.g. Maniatis et al., $Molecular$ $Cloning,$ Cold Spring Harbor Laboratory, Cold Spring Harbor, New York, 1982, which is incorporated by reference herein), to confer ampicillin-resistance or ampicillin- and kanamycin-resistance. The resulting colonies of cells which had undergone the transformation procedure were replica-plated onto MacConkey's agar (Difco) containing 2% xylose, 50 μg/ml ampicillin (Calbiochem) and 20 μg/ml kanamycin (Calbiochem). The results are given in Table I wherein xfe=transformants per μg and $(S/S_0)$=survival fraction compared to control ligation.

TABLE I

| | xfe Amp | xfe Kan + Amp | $(S/S_0)$ Amp + Kan |
|---|---|---|---|
| Control Lig. | — | $7 \times 10^4$ | 1 |
| 30' $HNO_2$ Treated | $8.5 \times 10^4$ | $4.4 \times 10^4$ | 0.628 |
| 60' $HNO_2$ Treated | $3.3 \times 10^4$ | $2.2 \times 10^4$ | 0.314 |
| 90' $HNO_2$ Treated | $1.4 \times 10^4$ | $2.6 \times 10^3$ | 0.037 |
| pXK23 | — | $5.4 \times 10^7$ | — |

Approximately 1% xylA mutants were obtained via partial marker cassette mutagenesis. Mutants which were distinguishable by virtue of having a stronger indication (i.e., a dark red color) on MacConkey's agar with 2% xylose. All colonies produced as a result of the transformations reported in Table I were lightly colored with the exception of mutant colonies denominated 7A, 7B and 8A. Mutant 7A was deposited as No. 53274 and mutant 8A was deposited as No. 53275 with the American Type Culture Collection, 12301 Parklawn Drive, Rockville, Md. on Sept. 27, 1985. It should be noted that although indicator plates containing MacConkey's agar plus 2% xylose were used for determining expression of xylA gene in $E.$ $coli,$ this protein may also be identified on a stained gel of soluble proteins or of whole boiled cells whereon xylose isomerase appears as a 44 Kda peptide.

EXAMPLE 2

Mutants produced with the aid of the constructions and methods of Example 1 were analyzed for synthesis of xylA protein and for xylose isomerase activity. The determination of xylose isomerase activity was made on equal amounts of dialyzed, cell-free extract (produced by sonication) which were incubated at various pH values and temperatures in the presence of 45% (w/v) D-glucose. The amount of fructose formation was determined by means of the cysteine-carbazole test [Dische, et al., $J.$ $Biol.$ $Chem.,$ 192, 583–587 (1951)] after 1 hour incubation. The background strain was RR1 containing either plasmid pXK23 or the mutant 7A plasmid. The amount of xylA protein synthesized was determined by examination of Coomassie Blue-stained [10% acetic acid; 45% methanol; 0.25% Coomassie Blue] 10% SDS-PAGE gels on which boiled cells which had been lysed by boiling in sample buffer [2% SDS; 62.5 mM Tris-HCl, pH 6.8; 10% glycerol; 5% β-mercaptoethanol] had been run.

As revealed on SDS-reducing gels of whole cell lysates (lysed in sample buffer as above) of the mutants, some of the mutants produce peptides smaller than 44 Kda, probably due to nonsense mutations within the structural gene. These cells producing protein products were discarded. Other cells produced full-length products.

Glucose isomerase (GI) activity, as determined in the cysteine-carbazole test, showed that the mutants 7A and 8A had a higher GI activity than wild type. That the 7A and 8A mutant-phenotypes were due to mutations on the plasmid was demonstrated by transformation of bacterial strain RR1 to the same phenotype using isolated plasmid.

$K_m$ and $V_m$ values were determined from the known amount of glucose added to measured concentrations of protein extracted from the transformed cells to produce a given absorbance at 560 nm at 0, 5, 10 and 20 min. in the cysteine-carbazole assay (indicative of the concentration of fructose). Plots of velocity versus time were made. Change in optical density was determined by subtracting the 0 time absorbance from the absorbance at later times. From the plots of velocity versus time, Lineweaver-Burke plots were made from which $K_m$ and $V_m$ were determined.

As illustrated in Table II, the approximate $K_m$ values of mutants 7A and 8A were better than the $K_m$ value of the wild type. In Table II: $K_m$ is the Michaelis-Menten constant, which is indicative of the degree to which glucose is isomerized to fructose by the corresponding enzyme; and $V_m$ is the maximum velocity of the reaction, which is indicative of the rate of conversion of glucose to fructose in the presence of the corresponding enzyme.

TABLE II

| Source | Reaction Constant for Glucose | |
|---|---|---|
| | $K_m$ | $V_m$ (per mg protein) |
| pXK23 | 0.21M | 0.082 |
| 7A | 0.073M | 0.032 |
| 8A | 0.028M | 0.040 |

Figure 3:
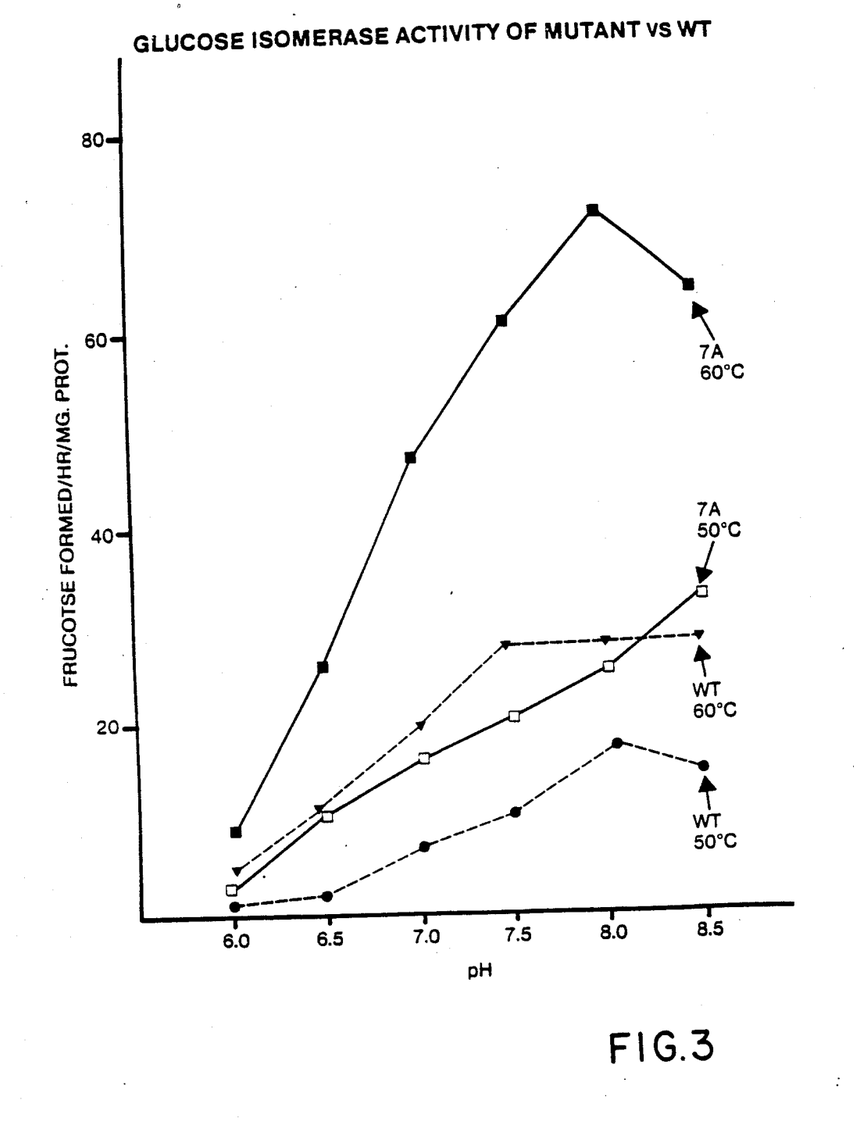
FIG. 3 is a graphic depiction of the glucose isomerase activity of xylose isomerase mutagenized according to the present invention as coplotted with the glucose isomerase activity of a wild type enzyme.

The formation of fructose from glucose was further analyzed at different pH values and temperatures. Equal amounts of cell-free extract were used in this experiment. Extracts were incubated at various pH values and temperature in the presence of 45% (w/v) D-glucose. Fructose was determined after 1 hour incubation. The background strain was RR1 containing either plasmid pXK23 or the mutant 7A plasmid. The results are illustrated in FIG. 3 for mutant 7A. As shown, mutant 7A exhibits twice the rate of isomerization of glucose exhibited by the "wild type" (strain RR1 containing plasmid pXK23). In addition, at 50° C. and at pH values lower than 7.0, the mutant exhibits a substantially higher isomerization rate than does the wild type.

EXAMPLE 3

Cultures of wild type E. coli and of mutants 7A and 8A were grown in LB medium [10 g/l Bacto-tryptone; 5 g/l Bacto-yeast extract; 5 g/l NaCl; pH adjusted to 7.5 with NaOH] containing 2% xylose and 50 μg/ml ampicillin, at various times samples were removed, lysed in a French press, and a 27,000×G supernatant fraction and a pellet fraction were obtained for each. The pellets were dissolved in 0.1% SDS and 10 mM Tris (pH 7.4) at room temperature. Portions of these extracts which represented equivalent numbers of cells were run on a 10% SDS-reducing gel.

Figure 4:
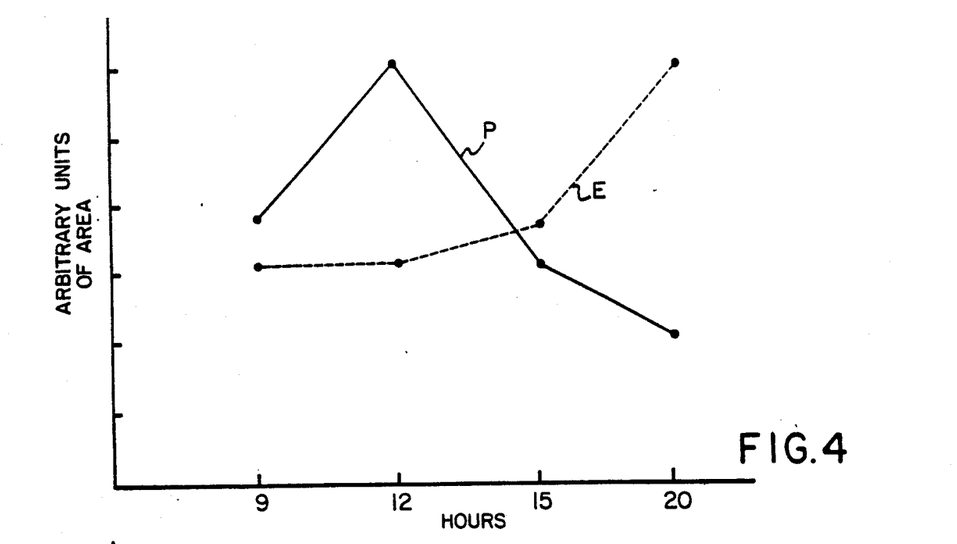
FIG. 4 is a graphic depiction of the amount and solubility of a first xylose isomerase mutant according to the present invention.
Figure 5:
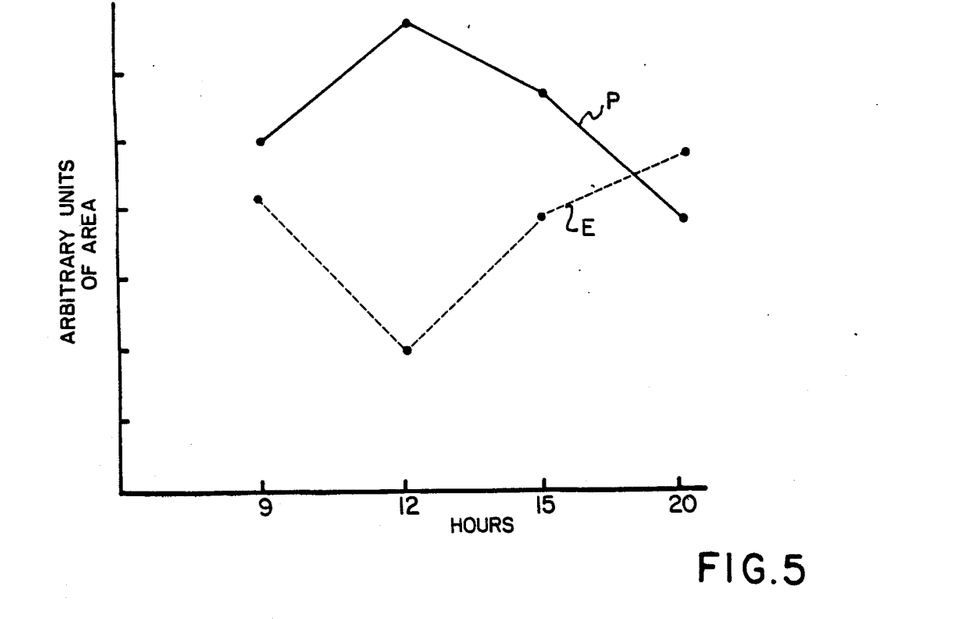
FIG. 5 is a graphic depiction of the amount and solubility of a second xylose isomerase mutant according to the present invention.

As a result of this experiment, it was determined that the mutant xylA proteins exhibited different solubilities inside the cell than does the wild type xylA protein. Normally, xylA protein, when induced on a pBR322 plasmid, accounts for about 20% of the cell protein and the xylA protein is all soluble. The mutant proteins are somewhat insoluble as shown in densitometer tracings of the SDS gels as illustrated FIGS. 4 (for mutant 7A) and 5 (for mutant 8A). The wild type plasmid exhibited mostly soluble xylA protein until 20 hours, while the mutants showed a high proportion of insoluble protein. As also shown in FIGS. 4 and 5, wherein lines labelled "P" correspond to xylA protein obtained from pelleted material and lines labelled "E" correspond to xylA protein obtained from supernatant fractions, the densitometer tracings of the SDS gels demonstrate that at 12 hours from 50 to 80% of the mutant protein was insoluble. However, with time the pellet material became more soluble.

In addition, it was determined from the gels that extracts did not contain more xylA protein than wild type. In fact, there was slightly less soluble protein in the mutants.

EXAMPLE 4

Various restriction fragments of plasmids isolated from mutants 7A and 8A were isolated using restriction endonucleases PvuII, PstI, XhoI and SalI (all obtained from BRL) and then were ligated to either plasmid pCF313 or to plasmid pXK23. The plasmids were transformed into E. coli cells of strain RR1 (for a characterization of this strain see e.g. Maniatis et al., supra) and the transformants were analyzed for their responses on MacConkey's agar plus 2% xylose. A darker indication was scored as a mutant and a lighter indication as wild type (W.T.). The results are shown in Table III.

TABLE III

| Mutant xylA Fragment Used | Recipient Wild-Type Plasmid | Response of Transformants | |
|---|---|---|---|
| | | 7A | 8A |
| PvuII [5' end] | pCF313 PvuII cut | W.T. | W.T. |
| PvuII [3' end] | pCF313 PvuII + PstI BAP | Mutant | Mutant |
| SalI [5' end] | Gel Purified pXK23 XhoI + SalI Large Frag. | Mutant | Mutant |

The mutations in 7A and 8A were located via the experiment the results of which are presented in Table I. These results indicate that the mutations are in the SalI to PvuII region of the xylA gene.

The 394 bp SalI to PvuII fragments of wild type 7A and 8A were isolated and cloned into the M13 phages mp18 and mp19 at the SmaI and SalI site. The fragments were sequenced in both orientations by the dideoxy sequencing procedures of Sanger, et al., Proc. Natl. Acad. Sci. (USA), 74, 5463-5467 (1972). One difference between the mutants 7A and 8A and the wild type was found. A transition from GC to At had occurred and had resulted in a change of a glu (GAG) residue to a lys (AAG) residue at amino acid position 262 in the protein. Substitution of an arginine residue at this position may produce a similar effect. Further sequencing of regions from SalI to the end of the gene and 200 bp 5' to the PvuII site (i.e., up to and including the base pair at position 278) did not pick up any other changes.

For mutants 7A and 8A, the change from glu to lys may bear on the insolubility problem observed in Example 3. The insolubility may be accounted for by an overall change in charge of the 7A and 8A proteins to the positive side which may cause these proteins to interact with DNA or with themselves such that precipitation occurs. The mutation changes a region of glu-lys-glu-ile-lys, which is charge balanced, to glu-lys-lys-ile-lys, which is not and which has a net +2 charge.

Although the present invention has been described in terms of preferred embodiments, it is expected that modifications and improvements will occur to those skilled in the art. For example, as illustrated in FIG. 6, the partial marker cassette of Example 1 may be cloned into an M13 phage, mp18. Thus two plasmid sources of partial marker cassette for xylose isomerase mutagenesis, mp128:SH and the plasmid vehicle pXK23.

Furthermore, although mutagenesis has been applied to the structural gene for xylose isomerase as an example in the present application, the constructions and methods according to the present invention may be applied to any nucleic acid as long as a method of selection for alterations or a screening method is available along with the isolated nucleic acid. Similarly, although a convenient HindIII site was available in the kanamycin resistance gene employed as the marker in the embodiment exemplified herein, any restriction site in any marker may be used as long as cleavage at the site results in the production of two nonfunctional portions of the marker gene, the function of which may be restored by ligation of the two portions at the site. If no site exists naturally in the marker, such a site may be introduced by site directed mutagenesis according to the procedures of Zoller et al., *Methods in Enzymol.*, 100, 468–500 (1983).

Moreover, although the partial marker exemplified herein comprises a kanamycin-resistance gene, other drug resistance markers, such as chloramphenicol resistance gene [Chang, et al., *J. Bacteriol.*, 134, 1141–1156 (1978)], or any marker for which an assay exists (e.g., markers which compensate for nutritional deficiencies such as trp or his auxotrophy) may be employed according to the present invention. Likewise, a partial marker cassette vector may not only be a bacterial plasmid but may include any of the following without limitation thereto: a phage vector [see e.g., Murray, et al., *Nature*, 251, 476 (1974)]; a cosmid vector [see e.g., Cattaneo, et al., *Nucleic Acids Res.*, 9, 2777 (1981)]; a yeast plasmid [see e.g., Livingston, *Genetics*, 86, 73–84 (1977)]; a yeast-bacterial shuttle vector [see e.g., Beggs, *Nature*, 275, 104–109 (1979)]; a viral vector [see e.g., Maeda, et al., *Nature*, 315, 592–594 (1985)]; or even a plant tumor-inducing plasmid [see e.g., Klee, et al., *BioTechnology*, 3, 637–642 (1985]. It is suggested in Schellenberg, et al., supra, for example, that because both *Saccharomyces cerevisiae* and *Schizosaccharomyces pombe* are xylose negative but are capable of fermenting xylose to ethanol, the cloning and expression of *E. coli* xylose isomerase may permit the construction of a xylose fermenting yeast strain.

As is well understood by those skilled in the art, in systems for the mutagenization of xylose isomerase such as the system disclosed herein, the host cells for manipulation of the partial marker cassette and vector may be any variant of *E. coli* strain K12 having the genotype (hsdR−, xylA−), such as the strains RR1 and JA221, as characterized in Maniatis, et al., supra employed herein.

It is also clear to those skilled in the art that mutant forms of xylose isomerase according to the present invention may be usefully employed in the glucose isomerase production of high-fructose syrups as described in Antrim et al., *Applied Biochemistry and Bioengineering*, 2, 93–155 (1979), and in Hemmingsen, *Applied Biochemistry and Bioengineering*, 2, 157–183 (1979), both of which disclose conditions for the isomerization of a monosaccharide such as glucose or xylose and both of which are incorporated by reference herein.

Accordingly, it is intended that the appended claims comprehend all such modifications and improvements as come within the scope of the invention as claimed.

We claim:

1. A structural gene which, when inserted in an appropriate vector used to transform an appropriate host, is capable of expressing an enzyme which isomerizes glucose to fructose and which is characterized by the presence of an adenosine residue at position 784 of the nucleotide sequence as given in [Table I] FIG. 7 and is also characterized as having a nucleotide sequence sufficiently similar to the nucleotide sequence of [Table I] FIG. 7 to permit said enzyme to isomerize glucose to fructose.

2. The structural gene as recited in claim 1 wherein said gene has a nucleotide sequence 3' to nucleotide position 298 which is identical to nucleotide sequence given in FIG. 7 3' to nucleotide position 297 except for the substitution of an adenosine residue for a guanidine residue at position 784.

3. The structural gene as recited in claim 1 wherein said gene comprises the mutant xylA gene as found in ATCC No. 53274.

4. The structural gene as recited in claim 1 wherein said gene comprises the mutant xylA gene as found in ATCC No. 53275.

5. A xylose isomerase enzyme characterized by the presence of a lysine residue amino acid position 262 and further characterized as being sufficiently similar in amino acid sequence to the amino acid sequence given in FIG. 7 to be capable of isomerizing glucose to fructose.

6. The xylose isomerase enzyme as recited in claim 5 wherein the amino acid sequence of said enzyme from amino acid residue 100 to the carboxyl terminus is identical to the amino acid sequence given in FIG. 7 except for the substitution of lys for glu at position 262.

7. The xylose isomerase enzyme as recited in claim 6 wherein said enzyme comprises the enzyme expression product of the plasmid-borne mutant xylA gene as found in ATCC No. 53274.

8. The xylose isomerase enzyme as recited in claim 6 wherein said enzyme comprises the enzyme expression product of the plasmid-borne mutant xylA gene as found in ATCC No. 53275.

9. A method for the isomerization of a monosaccharide comprising the step of exposing the monosaccharide to a xylose isomerase enzyme characterized by the presence of a lysine residue at position 262 of the amino acid sequence as given in FIG. 7 and further characterized as being sufficiently similar in amino acid sequence to the amino acid sequence given in FIG. 7 to be capable of isomerizing glucose to fructose under appropriate conditions for the isomerization of the monosaccharide.

10. The method for isomerization as recited in claim 9 wherein the amino acid sequence of said enzyme from amino acid residue 100 to the carboxyl terminus is identical to the amino acid sequence given in FIG. 7 except for the substitution of lys for glu at position 262.

11. The method for isomerization as recited in claim 9 wherein said enzyme comprises the enzyme expression product of the plasmid-borne mutant xylA gene as found in ATCC No. 53274.

12. The method for isomerization as recited in claim 11 wherein said monosaccharide is glucose.

13. The method for isomerization as recited in claim 11 wherein said monosaccharide is xylose.

14. The method for isomerization as recited in claim 9 wherein said enzyme comprises the expression product of the plasmid-borne mutant xylA gene as found in ATCC No. 53275.

15. The method for isomerization as recited in claim 14 wherein said monosaccharide is glucose.

16. The method for isomerization as recited in claim 14 wherein said monosaccharide is xylose.

* * * * *